(12) United States Patent
Kim et al.

(10) Patent No.: US 9,428,520 B2
(45) Date of Patent: Aug. 30, 2016

(54) DAPHNE GENKWA EXTRACTS, AND PHARMACEUTICAL COMPOSITION CONTAINING FRACTIONS OF THE EXTRACTS OR COMPOUNDS SEPARATED FROM THE EXTRACTS AS ACTIVE INGREDIENTS FOR PREVENTING OR TREATING ATOPIC DERMATITIS

(75) Inventors: Jae Wha Kim, Daejeon (KR); Kyung Seop Ahn, Daejeon (KR); Ho Bum Kang, Daejeon (KR); Sei Ryang Oh, Daejeon (KR); Jae Jong Go, Gyeonggi-do (KR); Joo Heon Kim, Daejeon (KR); Jang Mi Sun, Daejeon (KR); Jae Sung Song, Daejeon (KR); Hyun Woo Oh, Daejeon (KR); Da Jung Ji, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 132 days.

(21) Appl. No.: 14/117,737

(22) PCT Filed: May 17, 2012

(86) PCT No.: PCT/KR2012/003903
§ 371 (c)(1),
(2), (4) Date: Nov. 15, 2013

(87) PCT Pub. No.: WO2012/157978
PCT Pub. Date: Nov. 22, 2012

(65) Prior Publication Data
US 2014/0072664 A1 Mar. 13, 2014

(30) Foreign Application Priority Data

May 17, 2011 (KR) .................. 10-2011-0046274
May 17, 2012 (KR) .................. 10-2012-0052441

(51) Int. Cl.

| A61K 36/83 | (2006.01) |
|---|---|
| A61K 36/185 | (2006.01) |
| C07D 319/06 | (2006.01) |
| C07D 493/08 | (2006.01) |
| A61K 31/357 | (2006.01) |
| A61K 47/26 | (2006.01) |
| A61K 9/00 | (2006.01) |
| A61K 9/20 | (2006.01) |
| A61K 9/48 | (2006.01) |
| A23L 1/30 | (2006.01) |
| A23L 2/52 | (2006.01) |
| A23L 1/10 | (2006.01) |

(52) U.S. Cl.
CPC ............ *C07D 493/08* (2013.01); *A23L 1/1041* (2013.01); *A23L 1/3002* (2013.01); *A23L 2/52* (2013.01); *A61K 9/0019* (2013.01); *A61K 9/0095* (2013.01); *A61K 9/2018* (2013.01); *A61K 9/4858* (2013.01); *A61K 31/357* (2013.01); *A61K 36/83* (2013.01); *A61K 47/26* (2013.01); *A61K 2236/00* (2013.01)

(58) Field of Classification Search
None
See application file for complete search history.

(56) References Cited

FOREIGN PATENT DOCUMENTS

| CN | 1422623 A | 6/2003 |
|---|---|---|
| JP | 2004-83449 A | 3/2004 |
| JP | 2004083449 A * | 3/2004 |
| KR | 10-0840723 B1 | 6/2008 |
| KR | 10-2010-0115514 A | 10/2010 |

OTHER PUBLICATIONS

Viable Herbal Solutions (see cited website of www.arcive.org/web/20000124113842//http://viable-herbal.com/herboloby1/herbs42. copyrighted 1995,1997,1998,1999,2000, pp. 1-3).*

Lee, et al., "Meliae cortex extract exhibits anti-allergic activity through the inhibition of Syk kinase in mast cells", Toxicology and Applied Pharmacology, vol. 220, pp. 227-234, (2007).

Kai, et al., "Pharmacological Effects of Daphne genkwa and Chinese Medical Prescription, 'Jyu-So-To'", Yakugaku Zasshi, vol. 124, No. 6, pp. 349-354, (2004). English Abstract on first page and attached separately.

Pae, et al., "Review of Anti-Leukemia Effects from Medicinal Plants", Korean J. Oriental Physiology & Pathology, vol. 17, No. 3, pp. 605-610, (2003).

* cited by examiner

*Primary Examiner* — Chris R Tate
*Assistant Examiner* — Randall Winston
(74) *Attorney, Agent, or Firm* — Vorys, Sater, Seymour & Pease LLP; Mih Suhn Koh

(57) ABSTRACT

The present invention relates to a pharmaceutical composition for the prevention or treatment of atopy comprising the extract of *Daphne genkwa*, the fraction thereof, of the compound isolated from the same as an active ingredient. More precisely, the extract of *Daphne genkwa*, the fraction thereof, or the compound isolated from the same, genekwadapnin or yuanhuacine, of the present invention can increase the secretion of cytokine in Th1 immune cells and suppress atopy in the atopy mouse model, so that the extract of *Daphne genkwa*, the fraction thereof, or the compound isolated from the same of the present invention can be effectively used for the prevention or treatment of atopy.

3 Claims, 6 Drawing Sheets

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 1
ccatcaccat cttccaggag                                           20

<210> SEQ ID NO 2
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 2
acagtcttct gggtggcagt                                           20

<210> SEQ ID NO 3
<211> LENGTH: 20
<212> TYPE: DNA
<213> ORGANISM: Artificial Sequence
<220> FEATURE:
<223> OTHER INFORMATION: IL-2 forward primer

<400> SEQUENCE: 3
acctcaactc ctgccacaat                                           20

<210> SEQ ID NO 4
<211> LENGTH: 24
<212> TYPE: DNA
<213> ORGANISM: Artificial Sequence
<220> FEATURE:
<223> OTHER INFORMATION: IL-2 reverse primer

<400> SEQUENCE: 4
gcctgatatg ttttaagtgg gaag                                      24
```

<210> SEQ ID NO 5
<211> LENGTH: 20
<212> TYPE: DNA
<213> ORGANISM: Artificial Sequence
<220> FEATURE:
<223> OTHER INFORMATION: IL-4 forward primer

<400> SEQUENCE: 5
aatgggtctc acctcccaac                                               20

<210> SEQ ID NO 6
<211> LENGTH: 20
<212> TYPE: DNA
<213> ORGANISM: Artificial Sequence
<220> FEATURE:
<223> OTHER INFORMATION: IL-4 reverse primer

<400> SEQUENCE: 6
ttcagctcga acactttgaa                                               20

<210> SEQ ID NO 7
<211> LENGTH: 20
<212> TYPE: DNA
<213> ORGANISM: Artificial Sequence
<220> FEATURE:
<223> OTHER INFORMATION: IL-12 alpha forward primer

<400> SEQUENCE: 7
gaggcctgtt taccattgga                                               20

<210> SEQ ID NO 8
<211> LENGTH: 20
<212> TYPE: DNA
<213> ORGANISM: Artificial Sequence
<220> FEATURE:
<223> OTHER INFORMATION: IL-12 alpha reverse primer

<400> SEQUENCE: 8
agggacctcg cttttagga                                                20

<210> SEQ ID NO 9
<211> LENGTH: 20
<212> TYPE: DNA
<213> ORGANISM: Artificial Sequence
<220> FEATURE:
<223> OTHER INFORMATION: IL-15 forward primer

<400> SEQUENCE: 9
gaagccaact gggtgaatgt                                               20

<210> SEQ ID NO 10
<211> LENGTH: 20
<212> TYPE: DNA
<213> ORGANISM: Artificial Sequence
<220> FEATURE:
<223> OTHER INFORMATION: IL-15 reverse primer

<400> SEQUENCE: 10
ttgaaatgcc gagtgttttg                                               20

<210> SEQ ID NO 11
<211> LENGTH: 19
<212> TYPE: DNA
<213> ORGANISM: Artificial Sequence
<220> FEATURE:

```
<223> OTHER INFORMATION: IL-18 forward primer

<400> SEQUENCE: 11
gcaccccgga ccatattta                                                    19

<210> SEQ ID NO 12
<211> LENGTH: 20
<212> TYPE: DNA
<213> ORGANISM: Artificial Sequence
<220> FEATURE:
<223> OTHER INFORMATION: IL-18 reverse primer

<400> SEQUENCE: 12
gattacaggc gtgagccact                                                   20

<210> SEQ ID NO 13
<211> LENGTH: 20
<212> TYPE: DNA
<213> ORGANISM: Artificial Sequence
<220> FEATURE:
<223> OTHER INFORMATION: INF alpha forward primer

<400> SEQUENCE: 13
cctggtggtg ctcagctgca                                                   20

<210> SEQ ID NO 14
<211> LENGTH: 20
<212> TYPE: DNA
<213> ORGANISM: Artificial Sequence
<220> FEATURE:
<223> OTHER INFORMATION: INF alpha reverse primer

<400> SEQUENCE: 14
acctcccagg cacaagggct                                                   20

<210> SEQ ID NO 15
<211> LENGTH: 20
<212> TYPE: DNA
<213> ORGANISM: Artificial Sequence
<220> FEATURE:
<223> OTHER INFORMATION: INF gamma forward primer

<400> SEQUENCE: 15
tggctgaact gtcgccagca                                                   20

<210> SEQ ID NO 16
<211> LENGTH: 20
<212> TYPE: DNA
<213> ORGANISM: Artificial Sequence
<220> FEATURE:
<223> OTHER INFORMATION: INF gamma reverse primer

<400> SEQUENCE: 16
tggctgccta gttggccct                                                    20
```

DAPHNE GENKWA EXTRACTS, AND PHARMACEUTICAL COMPOSITION CONTAINING FRACTIONS OF THE EXTRACTS OR COMPOUNDS SEPARATED FROM THE EXTRACTS AS ACTIVE INGREDIENTS FOR PREVENTING OR TREATING ATOPIC DERMATITIS

BACKGROUND OF THE INVENTION

"The Sequence Listing submitted in text format (.txt) filed on Nov. 14, 2013, named "13fpo-10-12US_sequencinglist-.txt", created on Nov. 11, 2013, 3.50 KB), is incorporated herein by reference."

1. Field of the Invention

The present invention relates to a pharmaceutical composition for the prevention or treatment of atopy comprising the extract of *Daphne genkwa*, the fraction thereof, or the compound isolated from the same as an active ingredient.

2. Description of the Related Art

Atopy is a chronic relapsing dermatitis accompanying severe itch. Approximately 10~15% of children have atopic dermatitis, and 90% of them get presumably better naturally within 5 years of breakout. This atopic dermatitis is generally improved when patients become adults, and is not coming back at least outwardly in approximately 30~40% of them. However, the rest of them are still suffering dermatitis with such symptoms as dry skin, skin irritation and housewife's eczema whenever stimulated by irritants even as adults. Sensitive skin is characterized by low water retention, weak recovery power, hyperkeratinization, and itch, which therefore progresses easily to atopic skin.

The exact pathophysiology of atopy has not been completely understood, yet, and is only presumed to be attributed to genetic factors along with immunological and non-immunological mechanisms altogether. Most of atopy cases are extrinsic atopy, which is developed by IgE-related immune mechanism. There are many reports saying that delayed-type immune response caused by T-cell malfunction is responsible for this extrinsic atopy rather than specific allergen mediated immediate-type immune response. It has been recently reported that Th2 related cytokines including IL-4 which induce IgE generation from B cells are the causes of atopy (J S Kang et al., Inhibition of atopic dermatitis by topical application of silymarin in NC/Nga mice. intl immunopharm. (2008) 8. 1475-1480).

To treat atopy, ceramides, linoleic acids, vegetable oils or mineral oils, steroids including hydrocortisone, the materials which have been reinforced with anti-bacterial/anti-inflammatory activity, DNA synthesis inhibitors, cell hyper-proliferation inhibitors, and inflammation/itch suppressors have been proposed. However, the said materials can cause side-effects. For example, steroids can cause epidermal growth suppression, urea peroxides can cause over-irritation on skin, and antibiotics including anti-histamine agent can cause bacterial resistance and photosensitivity. Moreover, long-term administration of such drugs might bring more serious side effects such as telangiectasia and/or thickness of keratin. Gamma-linoleic acid, frequently used for relieving atopy these days (Korean Patent Publication No. 2000-0046633), is easily oxidized, indicating a problem of stability, and causes skin irritation strongly, so that it is not suitable for sensitive skin.

Therefore, natural substances have been focused recently to treat atopy, which are exemplified by *Artemisia vulgaris* extract (Korean Patent No. 10-0377262), the extract of *Ganoderma lucidum, Ulmus pumila*, Licorice, *Poria, Sesamurn indicum* L. and *Opuntia ficus* indica (Korean Patent No. 10-0517465), the extract of Evening primrose, *Aloe*, pyroligneous liquor, Violet, *Jujube*, pine mushroom, *Aralia elata, Panax ginseng*, green tea, *Eucommia ulmoides, Rubus coreanus, Schisandra chinensis, Artemisia vulgaris, Taraxacum mongolicum, Saururus chinensis, Astragalus membranaceus, Prunella vulgaris, Pinus thunbergii, Scutellaria baicalensis* and *Achyranthes japonica* (Korean Patent No. 10-0451444), the extract of blue *Perilla frutescens* and red *Perilla frutescens* (Korean Patent No. 10-0454752), the extract of *Castanea crenata, Coicis semen, Schisandra chinensis, Platycodon grandiflorum, Raphanus sativus, Liriope platyphylla* and *Acorus gramineus* (Korean Patent No. 10-0483539), the extract of lavender, *Eucalyptus globulus* and tea tree oil (Korean Patent No. 10-0597997), etc. *Loranthus parasiticus, Albizzia julibrissin, Xanthium strumarium*, and malt are also known to have an effect on atopy. However, these natural substances are weaker in treatment effect and even though they demonstrate some treatment effect they also cause allergic reaction especially on sensitive skin, which limits them in use.

Thus, it is highly requested to develop a safer and more effective substance than the conventional agents for the improvement and treatment of atopy.

In the course of study to screen a material that has an excellent effect in improving atopy from natural substances, the present inventors found out that the extract of *Daphne genkwa*, the fraction thereof, or genekwadapnin and yuanhuacine, the compounds isolated from the same, could increase the secretion of cytokine that converts Th1/Th2 imbalance resulted from atopic disease by acting on immune cells and epithelial cells, and further confirmed their effects on the improvement of atopy in the mouse model having atopic disease, leading to the completion of the present invention.

SUMMARY OF THE INVENTION

It is an object of the present invention to provide a pharmaceutical composition for the prevention or treatment of atopy comprising the extract of *Daphne genkwa*, the fraction thereof, or the compound isolated from the same as an active ingredient.

It is another object of the present invention to provide a cosmetic composition for the prevention or improvement of atopy comprising the extract of *Daphne genkwa*, the fraction thereof, or the compound isolated from the same as an active ingredient.

It is further an object of the present invention to provide a treatment method of atopy containing the step of administering a pharmaceutically effective dose of the extract of *Daphne genkwa*, the fraction thereof, or the compound isolated from the same to a subject having atopy.

It is also an object of the present invention to provide a prevention method of atopy containing the step of administering a pharmaceutically effective dose of the extract of *Daphne genkwa*, the fraction thereof, or the compound isolated from the same to a subject.

It is also an object of the present invention to provide a use of the extract of *Daphne genkwa*, the fraction thereof, or the compound isolated from the same as a pharmaceutical composition for the prevention and treatment of atopy.

It is also an object of the present invention to provide a use of the extract of *Daphne genkwa*, the fraction thereof, or the compound isolated from the same as a cosmetic composition for the prevention and improvement of atopy.

To achieve the above objects, the present invention provides a pharmaceutical composition for the prevention or treatment of atopy comprising the extract of *Daphne genkwa*, the fraction thereof, or the compound represented by formula 1 as an active ingredient.

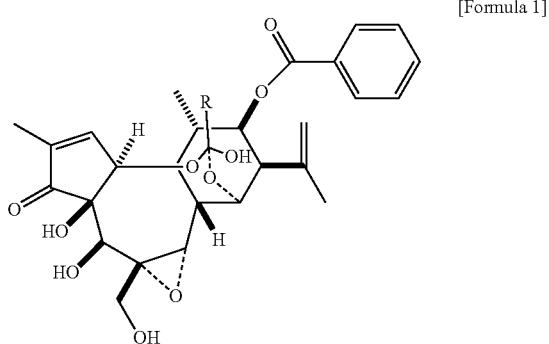

[Formula 1]

(Wherein,
R is —$C_6H_5$ or —CH=CHCH=CH$(CH_2)_4CH_3$.)

The present invention also provides a cosmetic composition for the prevention or improvement of atopy comprising the extract of *Daphne genkwa*, the fraction thereof, or the compound represented by formula 1, genekwadapnin (R=—$C_6H_5$) or yuanhuacine (R=—CH=CHCH=CH$(CH_2)_4$ $CH_3$), as an active ingredient.

The present invention also provides a treatment method of atopy containing the step of administering a pharmaceutically effective dose of the extract of *Daphne genkwa*, the fraction thereof, or the compound represented by formula 1 isolated from the same to a subject having atopy.

The present invention also provides a prevention method of atopy containing the step of administering a pharmaceutically effective dose of the extract of *Daphne genkwa*, the fraction thereof, or the compound represented by formula 1 isolated from the same to a subject.

The present invention also provides a use of the extract of *Daphne genkwa*, the fraction thereof, or the compound represented by formula 1 isolated from the same as a pharmaceutical composition for the prevention and treatment of atopy.

In addition, the present invention provides a use of the extract of *Daphne genkwa*, the fraction thereof, or the compound represented by formula 1 isolated from the same as a cosmetic composition for the prevention and improvement of atopy.

ADVANTAGEOUS EFFECT

As explained hereinbefore, the extract of *Daphne genkwa*, the fraction thereof, or the compound of formula 1 isolated from the same, genekwadapnin or yuanhuacine, of the present invention can increase the secretion of cytokine in Th1 immune cells and suppress atopy in the atopy mouse model, so that the extract of *Daphne genkwa*, the fraction thereof, or the compound of formula 1 isolated from the same of the present invention can be effectively used for the prevention or treatment of atopy.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
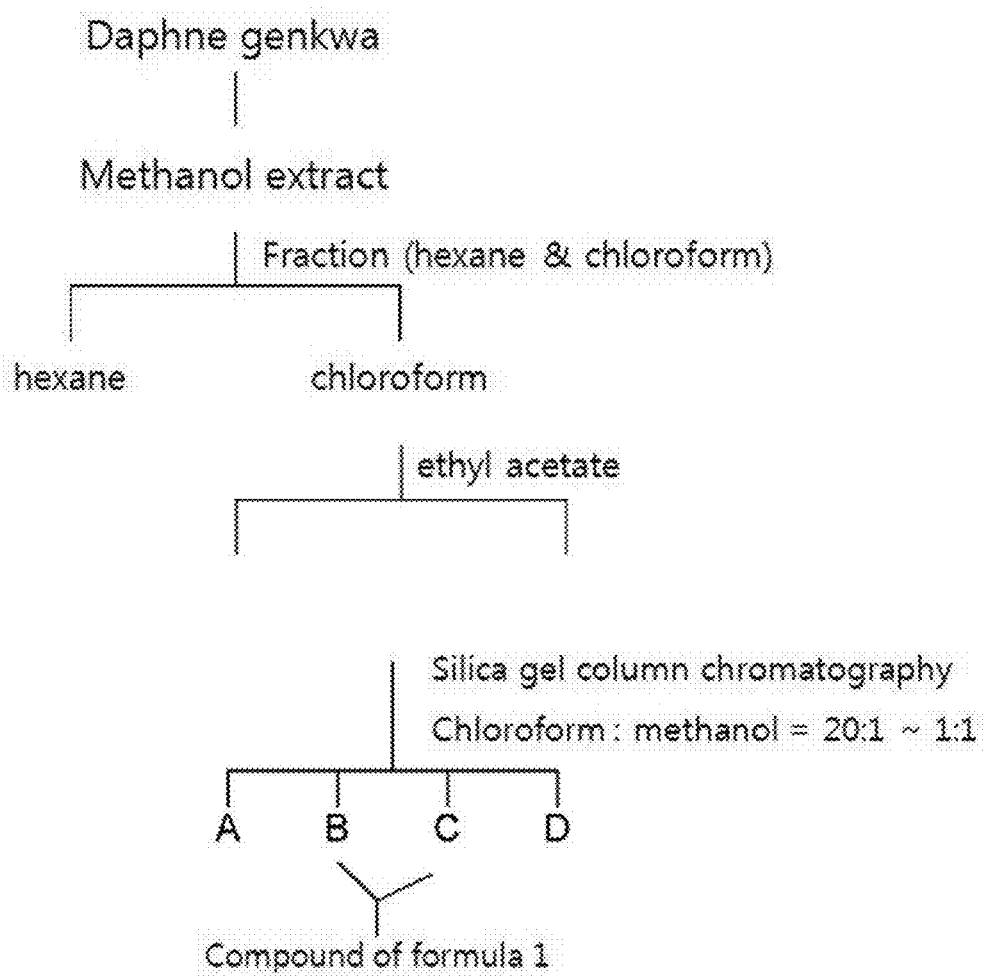
FIG. 1 is a diagram illustrating the fraction distribution chart according to an example of the present invention.

Hereinafter, the present invention is described in detail.

The present invention provides a pharmaceutical composition for the prevention or treatment of atopy comprising the extract of *Daphne genkwa* as an active ingredient.

To prepare the composition of the present invention, the *Daphne genkwa* is either grown or purchased.

The said *Daphne genkwa* extract can be preferably obtained from stems, roots, leaves, floral leaves or buds, and more preferably from floral leaves or buds.

To prepare the composition of the present invention, a solvent used for the extraction of *Daphne genkwa* is not limited as long as it can be appropriate for the extraction of natural substance, but preferably selected from the group consisting of methanol, methanol aqueous solution, ethanol, ethanol aqueous solution, butanol, acetone, or a mixture thereof, and more preferably methanol.

The volume of the extraction solvent is preferably 2~200 times the weight of *Daphne genkwa*, and more preferably 10~30 times, but not always limited thereto.

The method for the extraction of *Daphne genkwa* is preferably selected from the conventional extraction methods well known to those in the art, which are exemplified by those using extraction device such as hot-water extraction, soaking extraction, supercritical extraction, subcritical extraction, high temperature extraction, high pressure extraction, reflux extraction, and ultrasonification extraction or those using adsorption resin like XAD and HP-20. It is also preferred to extract by reflux extraction with raising temperature or at room temperature. The preferable temperature for the extraction is 10~30° C. and the preferable time for the extraction is 1~20 days, more preferably 5~10 days, but not always limited thereto.

The present invention also provides a pharmaceutical composition for the prevention or treatment of atopy comprising the fraction of *Daphne genkwa* extract as an active ingredient.

The fraction of the present invention can be obtained by the method comprising the following steps:
obtaining *Daphne genkwa* extract by adding water, $C_1$~$C_4$ lower alcohol, or the mixture thereof to *Daphne genkwa* (step 1); and obtaining fractions by fractionation of the extract obtained in step 1 by using hexane, chloroform, and ethyl acetate (step 2).

The preparation method mentioned above can be illustrated in more detail, step by step, hereinafter.

First, step 1 is to obtain *Daphne genkwa* extract by using an extraction solvent.

The *Daphne genkwa* extract can be obtained by the preparation method described above.

Next, step 2 is to obtain fractions by performing fractionation of the extract obtained in step 1 with hexane, chloroform, and ethyl acetate.

Particularly, to obtain the fractions, the *Daphne genkwa* extract obtained in step 1 (1.5 kg) was suspended in water, to which hexane, chloroform, and ethyl acetate were added stepwise. After separating each layer, chloroform layer was concentrated under reduced pressure and then dried to give chloroform fraction (150 g) and ethyl acetate fraction (164 g).

At this time, the concentration under reduced pressure can be performed preferably by using rotary evaporator, but not always limited thereto. The drying process herein can be preferably performed by reduced pressurized drying, vacuum drying, boiling drying, spray drying, room temperature drying, or freeze drying, and more preferably performed by freeze drying, but not always limited thereto.

In addition, the present invention provides a pharmaceutical composition for the prevention or treatment of atopy comprising the compound represented by formula 1 as an active ingredient:

[Formula 1]

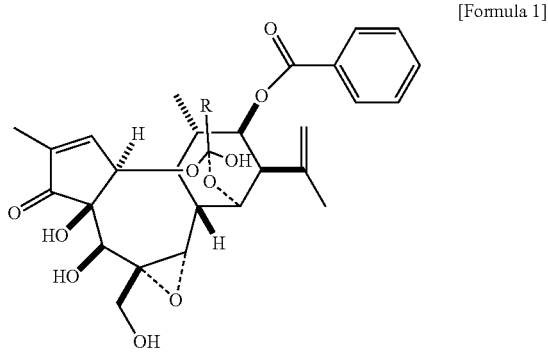

(Wherein,
R is —$C_6H_5$ or —CH═CHCH═CH($CH_2$)$_4CH_3$.)

In the compound of formula 1, when R is —$C_6H_5$, the compound is genekwadapnin. In the meantime, when R is —CH═CHCH═CH($CH_2$)$_4CH_3$, the compound is yuanhuacine.

The compound of formula 1, genekwadapnin or yuanhuacine, can be obtained by the following steps: extracting *Daphne genkwa* extract, fractionating thereof, separating and purifying the compound from the *Daphne genkwa* chloroform fraction by using silica gel column chromatography.

Particularly, the said silica gel column chromatography is preferably performed one or a few times repeatedly. As a moving phase, chloroform:methanol (99:1~1:1) is preferably used. At this time, the solvent can be eluted by density gradient elution which turns non-polarity to polarity stepwise. Atopy treating effect of the collected fractions was measured to select an active fraction.

Figure 2:
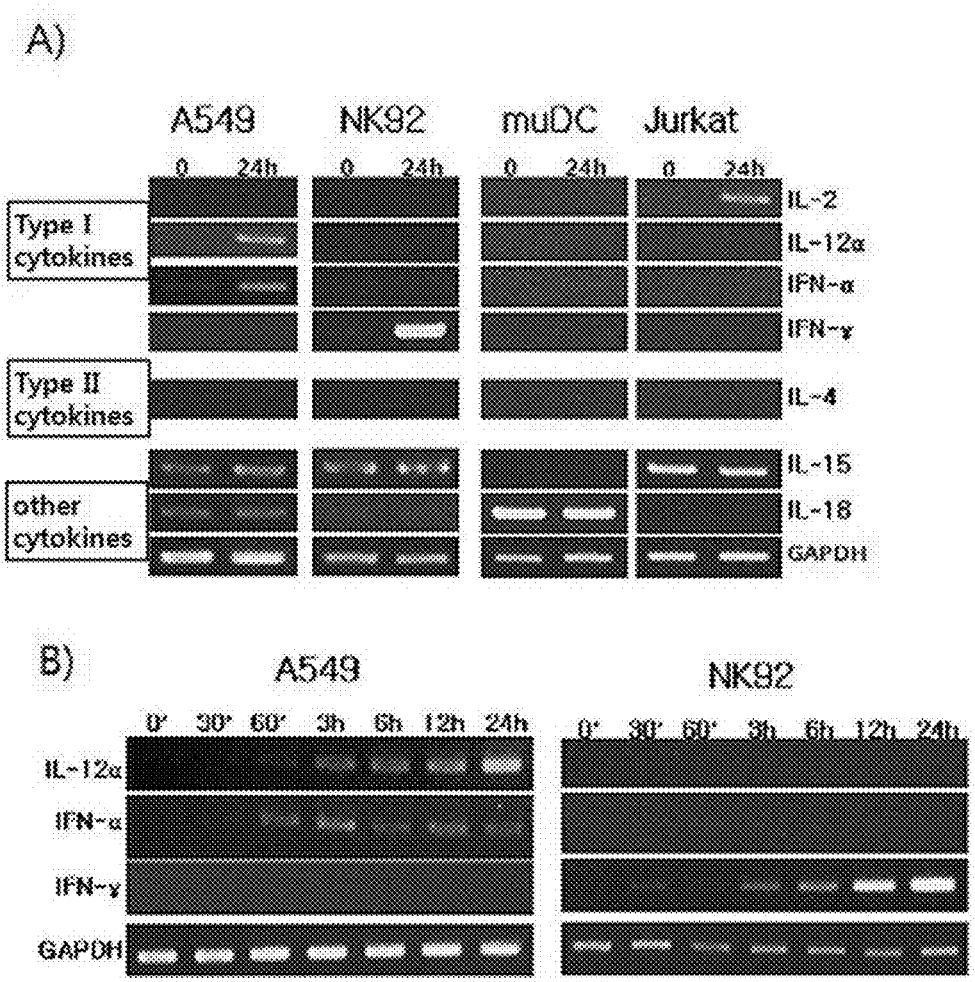
FIG. 2 is a diagram illustrating the results of RT-PCR performed to investigate the changes of mRNA levels of Type 1 and Type II cytokines according to an example of the present invention.

The *Daphne genkwa* extract, the fraction thereof, or the compound isolated from the same of the present invention was confirmed to increase the secretion of cytokine in Th1 immune cells (see FIG. 2), and to suppress atopy in the atopy mouse model (see FIG. 3 and FIG. 4), suggesting that the extract, the fraction, or the compound of the present invention can be effectively used for the prevention or treatment of atopy.

The *Daphne genkwa* extract, the fraction thereof, or the compound represented by formula 1 (genekwadapnin or yuanhuacine) of the present invention can be preferably included in the pharmaceutical composition of the invention at the volume of 0.1~50 weight %, but not always limited thereto.

The present invention also provides a cosmetic composition for the prevention or improvement of atopy comprising the extract of *Daphne genkwa*, the fraction thereof, or the compound isolated from the same, genekwadapnin or yuanhuacine, as an active ingredient.

The present invention also provides a preparation for skin external application for the prevention or treatment of atopy comprising the extract of *Daphne genkwa*, the fraction thereof, or the compound isolated from the same, genekwadapnin or yuanhuacine, as an active ingredient.

In addition, the present invention provides a health functional food for the prevention or improvement of atopy comprising the extract of *Daphne genkwa*, the fraction thereof, or the compound isolated from the same, genekwadapnin or yuanhuacine, as an active ingredient.

The pharmaceutical composition of the present invention can additionally contain proper carriers, excipients and diluents generally used for the preparation of drugs.

The pharmaceutical composition of the present invention can be formulated for oral administration, for example powders, granules, tablets, capsules, suspensions, emulsions, syrups and aerosols, and for parenteral administration, for example external use, suppositories and sterile injections, etc. The carriers, excipients and diluents are exemplified by lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil. Formulations can be prepared by using generally used excipients or diluents such as fillers, extenders, binders, wetting agents, disintegrating agents and surfactant. The pharmaceutical composition of the present invention can be prepared for oral or parenteral administration by mixing with generally used diluents or excipients such as fillers, extenders, binders, wetting agents, disintegrating agents and surfactants. Solid formulations for oral administration are tablets, pills, powders, granules and capsules. These solid formulations are prepared by mixing the composition of the present invention with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The pharmaceutical composition of the present invention can be administered orally or parenterally (for example, intravenous, hypodermic, peritoneal, or local injection). The effective dosage of the composition can be determined according to patient condition, weight, age, gender, diet, excretion, disease severity, administration method, administration pathway, and administration period, etc. The dosage of the freeze-dried extract or fraction of the present invention is 0.0001~500 mg/kg per day and preferably 0.001~100 mg/kg per day, and administration frequency is once a day or preferably a few times a day.

The pharmaceutical composition of the present invention can be administered alone or together with surgical operation, hormone therapy, chemo-therapy and biological regulators.

The cosmetic composition of the present invention can be formulated as skin lotion, skin softener, skin toner, astringent, lotion, milk lotion, moisture lotion, nutritive lotion, massage cream, nutritive cream, moisture cream, hand cream, essence, nutritive essence, pack, soap, shampoo, cleansing foam, cleansing lotion, cleansing cream, body lotion, body cleanser, milk lotion, press powder, loose powder, eye shadow, etc.

The cosmetic composition of the present invention can include, in addition to the *Daphne genkwa* extract of the present invention, a supplement generally used in the field of cosmetics such as fatty substance, organic solvent, resolvent, concentrate, gelling agent, softener, antioxidant, suspending agent, stabilizer, foaming agent, odorant, surfactant, water, ionic or non-ionic emulsifying agent, filler, sequestering agent, chelating agent, preserving agent, vitamin, blocker, moisturizing agent, essential oil, dye, pigment, hydrophilic or hydrophobic activator, lipid vesicle or other components generally used in cosmetics.

The *Daphne genkwa* extract of the present invention can be formulated as a preparation for skin external application. The preparation for skin external application containing the *Daphne genkwa* extract of the present invention can additionally include a supplement generally used in the field of skin science such as fatty substance, organic solvent, resolvent, concentrate, gelling agent, softener, antioxidant, suspending agent, stabilizer, foaming agent, odorant, surfactant, water, ionic or non-ionic emulsifying agent, filler, sequestering agent, chelating agent, preserving agent, vitamin, blocker, moisturizing agent, essential oil, dye, pigment, hydrophilic or hydrophobic activator, lipid vesicle or other components generally used in a preparation for skin external application. The amount of the above supplement can be determined as generally accepted in the field of skin science.

The *Daphne genkwa* extract of the present invention can be used as a health functional food. The food herein is not limited. For example, the *Daphne genkwa* extract can be added to drinks, meat, sausages, bread, biscuits rice cakes, chocolates, candies, snacks, cookies, pizza, ramyuns, flour products, gums, dairy products including ice cream, soups, beverages, alcohol drinks and vitamin complex, etc, and in wide sense, almost every food applicable in the production of health food can be included.

The *Daphne genkwa* extract of the present invention can be added as it is or as mixed with other food components according to the conventional method. The mixing ratio of active ingredients can be regulated according to the purpose of use (prevention or improvement). In general, to produce health food or beverages, the *Daphne genkwa* extract of the present invention is added preferably by 0.1~90 weight part to the total food weight. However, if long term administration is required for health and hygiene or regulating health condition, the content can be lower than the above but higher content can be accepted as well since the *Daphne genkwa* extract of the present invention has been proved to be very safe.

The composition for health beverages of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and glucose alcohols such as xilytole, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. The content of the natural carbohydrate is preferably 1~20 g and more preferably 5~12 g in 100 ml of the composition.

In addition to the ingredients mentioned above, the *Daphne genkwa* extract of the present invention can include in variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The *Daphne genkwa* extract of the present invention can also include natural fruit juice, fruit beverages and/or fruit flesh addable to vegetable beverages. All the mentioned ingredients can be added singly or together. The mixing ratio of those ingredients does not matter in fact, but in general, each can be added by 0.1~20 weight part per 100 weight part of the *Daphne genkwa* extract of the invention.

The present invention also provides a treatment method of atopy containing the step of administering a pharmaceutically effective dose of the extract of *Daphne genkwa*, the fraction thereof, or the compound isolated from the same, genekwadapnin or yuanhuacine, to a subject having atopy.

The present invention also provides a treatment method of atopy containing the step of administering a pharmaceutically effective dose of the extract of *Daphne genkwa*, the fraction thereof, or the compound isolated from the same, genekwadapnin or yuanhuacine, to a subject.

The *Daphne genkwa* extract, the fraction thereof, or the compound isolated from the same of the present invention was confirmed to increase the secretion of cytokine in Th1 immune cells (see FIG. 2), and to suppress atopy in the atopy mouse model (see FIG. 3 and FIG. 4), suggesting that the extract, the fraction, or the compound of the present invention can be effectively used for the prevention or treatment method of atopy.

The present invention also provides a use of the extract of *Daphne genkwa*, the fraction thereof, or the compound of formula 1 isolated from the same as a pharmaceutical composition for the prevention and treatment of atopy.

The present invention also provides a use of the extract of *Daphne genkwa*, the fraction thereof, or the compound of formula 1 isolated from the same as a cosmetic composition for the prevention and improvement of atopy.

The *Daphne genkwa* extract, the fraction thereof, or the compound isolated from the same of the present invention was confirmed to increase the secretion of cytokine in Th1 immune cells (see FIG. 2), and to suppress atopy in the atopy mouse model (see FIG. 3 and FIG. 4), suggesting that the extract, the fraction, or the compound of the present invention can be effectively used for the prevention or treatment method of atopy.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

EXAMPLE 1

Separation of Genekwadapnin and Yuanhuacine 11.7 kg of the dried buds of *Daphne genkwa* was loaded in 20 L of methanol, followed by extraction three times to give 1.5 kg of methanol extract. The obtained methanol extract was suspended in 10 L of water, followed by extraction three times stepwise with 10 L of each n-hexane, chloroform, and ethyl acetate as solvents. As a result, 323 g of hexane fraction, 150 g of chloroform fraction, and 164 g of ethyl acetate fraction were obtained. Among them, 74 g of chloroform fraction was loaded on silica gel column, followed by elution with chloroform and methanol (density gradient of 99:1~1:1). As a result, 20 g of subtraction was obtained, which was loaded again on reversed phase silica gel column. The mixed solution of methanol and water (7:3) was used to give 1.1 g of genekwadapnin containing fraction and 1.4 g of yuanhuacine containing fraction. 1.1 g of the genekwadapnin containing fraction was loaded on normal phase silica gel column (elution solvent: n-hexane and ethyl acetate, 15:1) to give 208.7 mg of active fraction. The obtained active fraction was purified by reversed phase silica gel column chromatography (elution solvent: methanol and water, 3:1) to give 125.6 mg of genekwadapnin compound. Normal phase silica gel column chromatography (elution solvent: n-hexane and ethyl acetate, 9:1~0:100) and methanol solvent recrystallization were performed with 1.4 g of yuanhuacine fraction. As a result, 74 mg of yuanhuacine was obtained.

EXAMPLE 2

Cell Culture

Human cell lines (A549, NK92, muDC, Jurkat) were cultured in a 37° C., 5% $CO_2$ humidified incubator.

Particularly, NK92 (human NK lymphoma), the IL-2 dependent NK cell line, was purchased from ATCC (American Type Culture Collection). The NK92 cell line was maintained in α-MEM (Life Technologies, Karlsruhe, Germany) supplemented with 20% FCS (HyClone, Logan, Utah), 2 mM L-glutamate, 100 μg/ml penicillin, 100 μg/ml streptomycin (Life Technologies) and 100 U/ml IL-2 (Chiron, Emeryville, Calif.).

EXPERIMENTAL EXAMPLE 1

RT-PCR

RT-PCR was performed to investigate the changes of mRNA levels in relation to the inducement of IFN-γ, IL-2, and IL-12 in A549, NK92, muDC, and Jurkat cells cultured in <Example 2>. These cells were cultured in the presence of 2 ng of genekwadapnin or yuanhuacine for 12 hours.

Phase II RT-PCR was performed with oligo-dT primer, reverse transcriptase, specific primer set, and Taq polymerase (Takara, Shiga, Japan). Total RNA was isolated according to the standard protocol. cDNA was synthesized by using Accusript High Fidelity 1st Strand cDNA Synthesis Kit (Stratagene) according to the manufacturer's instruction. 1 μl of the synthesized cDNA was used for PCR with 20 μl of reaction mixture containing 0.5 U ExTaq DNA polymerase, 1× buffer, 1 mM dNTP mix (Takara) and specific primer set. PCR amplification was performed using GeneAmp PCR system 2700 (Applied Biosystems, Foster city, CA, USA) as follows: predenaturation at 94° C. for 5 minutes, denaturation at 94° C. for 45 seconds, annealing at 56° C. for 45 seconds, polymerization at 72° C. for 1 minute, 25~40 cycles from denaturation to polymerization, and final extension at 72° C. for 7 minutes. PCR primers shown in [Table 1] were designed by using Primer 3 program, which were purchased from Bioneer (Daejeon, Korea). At this time, GAPDH was used as the internal control.

TABLE 1

| Name | Forward | Reverse |
|---|---|---|
| GAPDH | CCATCACCATCTTCCAGGAG (SEQ. ID. NO: 1) | ACAGTCTTCTGGGTGGCAGT (SEQ. ID. NO: 2) |
| IL-2 | ACCTCAACTCCTGCCACAAT (SEQ. ID. NO: 3) | GCCTGATATGTTTTAAGTGGGAAG (SEQ. ID. NO: 4) |
| IL-4 | AATGGGTCTCACCTCCCAAC (SEQ. ID. NO: 5) | TTCAGCTCGAACACTTTGAA (SEQ. ID. NO: 6) |
| IL-12α | GAGGCCTGTTTACCATTGGA (SEQ. ID. NO: 7) | AGGGACCTCGCTTTTTAGGA (SEQ. ID. NO: 8) |
| IL-15 | GAAGCCAACTGGGTGAATGT (SEQ. ID. NO: 9) | TTGAAATGCCGAGTGTTTTG (SEQ. ID. NO: 10) |
| IL-18 | GCACCCCGGACCATATTTA (SEQ. ID. NO: 11) | GATTACAGGCGTGAGCCACT (SEQ. ID. NO: 12) |
| IFNα | CCTGGTGGTGCTCAGCTGCA (SEQ. ID. NO: 13) | ACCTCCCAGGCACAAGGGCT (SEQ. ID. NO: 14) |
| IFNγ | TGGCTGAACTGTCGCCAGCA (SEQ. ID. NO: 15) | TGGCTGCCTAGTTGGCCCCT (SEQ. ID. NO: 16) |

The PCR product was electrophoresed on 1.5% agarose gel, which was stained with ethidium bromide (EtBr) and then visualized by using Gel Doc 2000 UV trans-illuminator (Bio-Rad Laboratories, Hercules, Calif., UV). Analysis was performed with Quantity One software (Bio-Rad Laboratories). Each sample was tested at least three times and the results are shown in FIGS. 2A and 2B.

As a result, as shown in FIG. 2A, the transcripts of Type I cytokines, IFN-γ, IL-2, and IL-12, were significantly increased in NR92 and A549 cells 12 hours after being treated with genekwadapnin or yuanhuacine, while the transcript of type II cytokine, IL-4, was not induced. In the meantime, the transcripts of IL-15 and IL-18 were not controlled (FIG. 2A). As shown in FIG. 1B, the action of genekwadapnin or yuanhuacine to induce IL-12 and IFN-γ was induced within 3 hours at transcriptional level (FIG. 1B).

EXPERIMENTAL EXAMPLE 2

Atopy Treatment Effect of Genekwadapnin or Yuanhuacine in Atopy Mouse Model <2-1> Atopy Treatment Effect in NC Mouse Model NC mouse is the mouse showing typical atopy symptom when it is raised in the conventional space. Genekwadapnin or yuanhuacine was spread locally on NC mouse starting to show atopy symptom, followed by observation of changes of atopy symptom. To minimize errors among mice and to confirm the treatment effect, each mouse was treated locally and skin tissues proceeded to biopsy to prove the atopy treatment effect experimentally.

Figure 3:
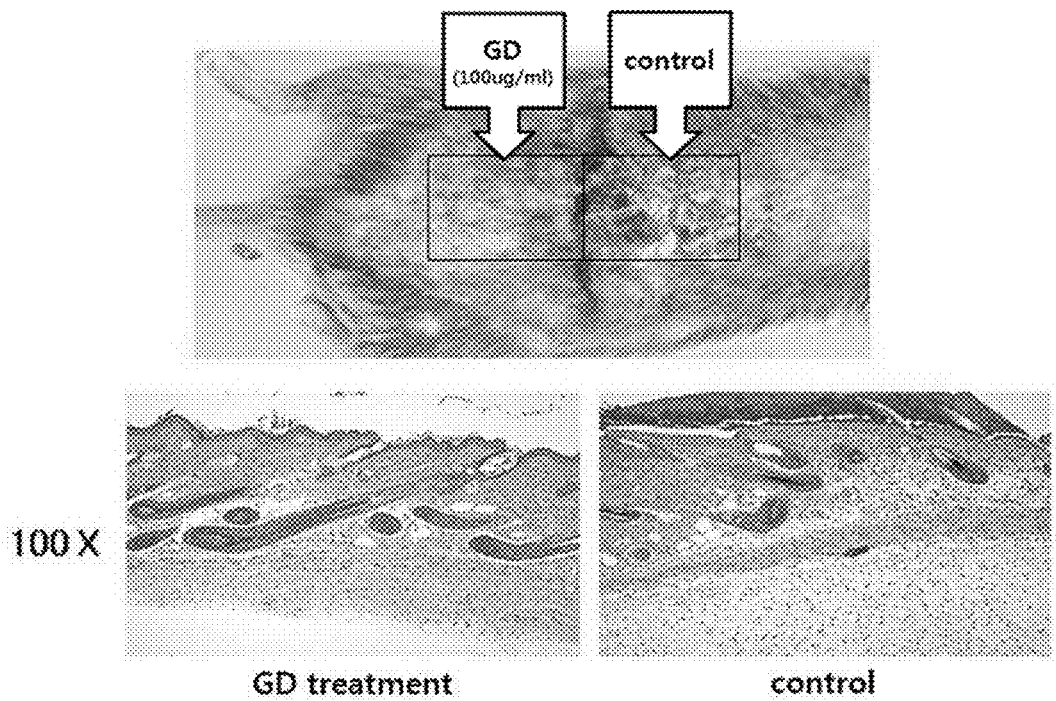
FIG. 3 is a diagram illustrating the atopy treatment effect in the atopy mouse model according to an example of the present invention:
GD: genekwadapnin treated group; and
control: control group.

As a result, as shown in FIG. 3, on the back where genekwadapnin or yuanhuacine was spread, atopy symptom was significantly reduced. The biopsy with those skin tissues also demonstrated significant difference in the distribution of inflammatory cells, which was that the area treated with genekwadapnin or yuanhuacine exhibited almost normal phenotype (FIG. 3).

<2-2> Confirmation of Atopy Treatment Effect in Atopy Induced Mouse Model

Figure 4:
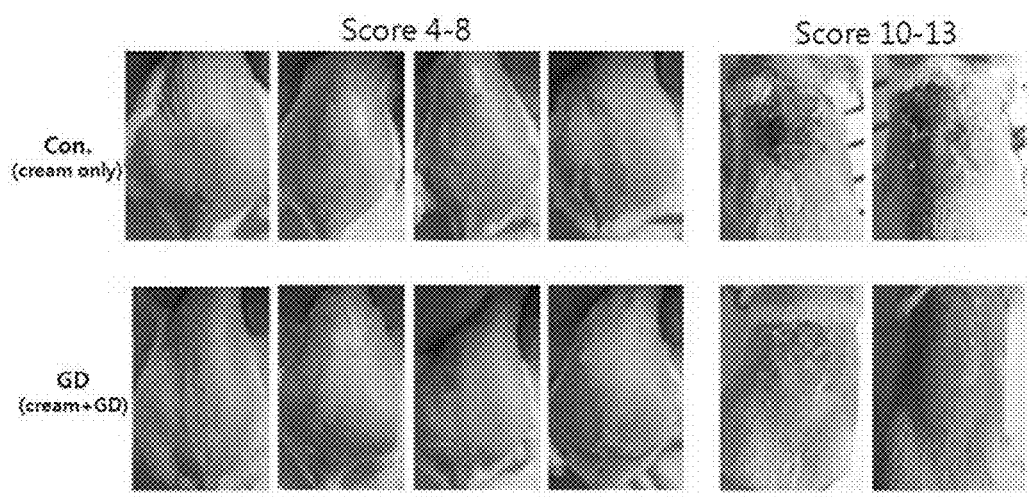
FIG. 4 is a diagram illustrating the atopy treatment effect in the atopy induced mouse according to an example of the present invention.

DNCB, one of allergens, was spread on the shaved skin of a normal Balb/C mouse to induce atopy intentionally. Atopy symptoms varied from the dose of DNCB and the treatment period, which were classified into different score groups (score 4~8 group and score 10~13 group). In the mouse group (score 4~8 group) which was treated with a lower dose of DNCB, atopic skin was recovered to normal skin within 24 hours from the treatment of genekwadapnin or yuanhuacine. On the other hand, even in the mouse group of score 10~13 which showed severe atopic symptoms, the speed of recovery was at least two times faster than the control group (FIG. 4). At that time, the test was performed in duplicate with 10 mice each.

Therefore, it was confirmed that the *Daphne genkwa* extract, and the compounds isolated therefrom, genekwadapnin and yuanhuacine, of the present invention were effective in preventing or treating atopy.

<2-3> Confirmation of Atopy Treatment Effect in Atopy Patient

After spreading genekwadapnin or yuanhuacine on the skin of atopy patients, atopy treatment effect of the compound was confirmed.

Particularly, 5 ug/ml of genekwadapnin or yuanhuacine was spread on the skin of atopy patients, followed by observation for 5~20 days. The treatment effect was confirmed by Medream Skin Clinic (Goejeong-dong, Seogu, Daejeon, Korea).

Figure 5:
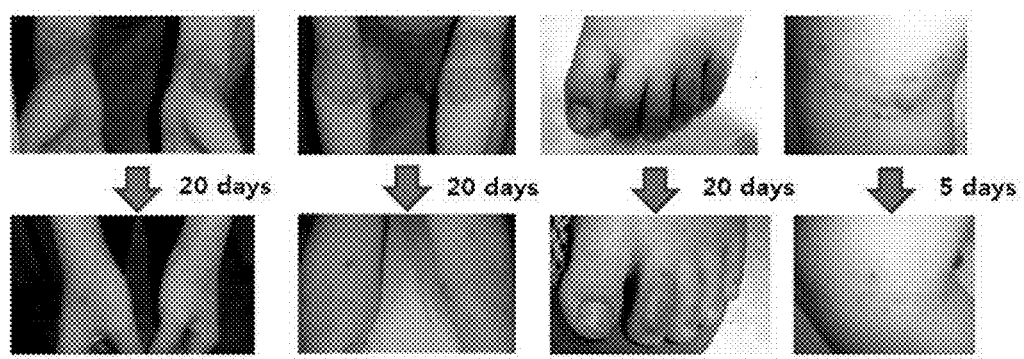
FIG. 5 is a diagram illustrating the atopy treatment effect in the atopy patient according to an example of the present invention.

As a result, as shown in FIG. 5, in the atopy patient spread with genekwadapnin or yuanhuacine, the atopic skin was recovered to normal 5 days after the treatment when the symptoms were minor, or the atopic skin was recovered to normal 20 days after the treatment when the symptoms were severe (FIG. 5).

<2-3> Intracellular Mechanism of Genekwadapnin or Yuanhuacine

To investigate the intracellular mechanism of genekwadapnin or yuanhuacine, the NK92 cells cultured in <Example 2> were treated with genekwadapnin or yuanhuacine at the concentration of 500 ng/ml. 12 hours later, phosphorylation level of PKC isotype was investigated by using antibodies. The quantity of protein used herein was confirmed by using GAPDH.

Particularly, the cells treated with genekwadapnin or yuanhuacine were dissolved in ice by using cold SDS-lysis buffer [(50 mM HEPES, 150 mM NaCl, 0.2 mM EDTA, 0.5% NP-40, 0.1% SDS, 1 mM Na3VO4, 10 mM NaF, and complete Protein Inhibitor Cocktail (Roche)] for 30 minutes. The dissolved cell solution was spinned at the speed of 13,000 rpm for 30 minutes in a high-speed rotating machine to precipitate insoluble part and then water soluble part was separated. The separated cell aqueous solution was quantified, followed by electrophoresis using 10~20% SDS-PAGE. Cellular protein separated on the gel was transcribed onto PVDF membrane (Millipore, Billerica, Mass., USA) at 100 V for 2 hours. To confirm PCK isotype phosphorylated in the cells, poly rabbit anti-PKD1, -phosphoPKD1 (Ser916), -phosphoPKD1 (Ser744/748), -phosphoPKCα/βII, -phosphoPKCδ, -phosphoPKCθ, and -phosphoPKCζ/λ IgG (Cell signaling Technology, USA) (1:1000) were used as primary antibodies. As a secondary antibody, horseradish peroxidase peroxidase-conjugated goat anti-rabbit IgG (Santa Cruz Biotechnology, USA) (1:3000) was treated at room temperature for 60 minutes. To confirm the equal amount of cellular protein, poly rabbit anti-GAPDH IgG (Santa Cruz Biotechnology, Pasadena, Calif., USA) was used. Upon completion of the immune reaction, the membrane was reacted with ECL reagent (Millipore, Billerica, Mass., USA), which was then exposed on X-ray film in order to observe the phosphorylation level of PKC isotype exhibited as a band on the film.

Figure 6:
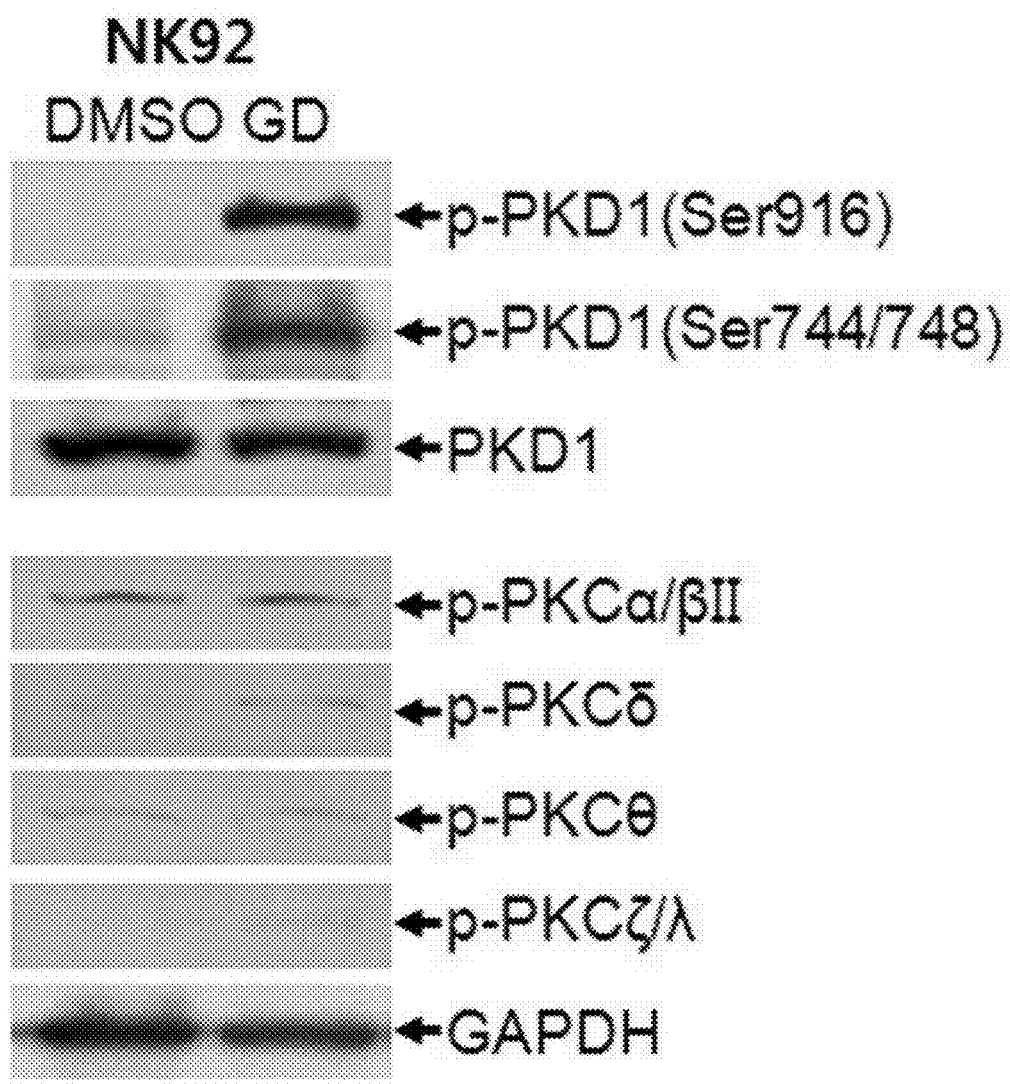
FIG. 6 is a diagram illustrating the intracellular mechanism according to an example of the present invention:
GD: genekwadapnin treated group or yuanhuacine treated group.

As a result, as shown in FIG. 6, in NK92 cells, the cells treated with genekwadapnin or yuanhuacine, PKD1 level was not changed but phosphorylation of serin residues ($744^{th}/748^{th}$, and $916^{th}$ sites of PKD1 protein) was confirmed. In the meantime, it was confirmed that other types of PCK isotype were not phosphorylated (FIG. 6).

The Manufacturing Examples of the composition for the present invention are described hereinafter.

MANUFACTURING EXAMPLE 1

Preparation of Pharmaceutical Formulations

<1-1> Preparation of Powders

| | |
|---|---|
| *Daphne genkwa* extract, fraction thereof, or compound isolated from the same | 20 mg |
| Lactose | 20 mg |

Powders were prepared by mixing all the above components, which were filled in airtight packs according to the conventional method for preparing powders.

<1-2> Preparation of Tablets

| | |
|---|---|
| *Daphne genkwa* extract, fraction thereof, or compound isolated from the same | 20 mg |
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| | |
|---|---|
| *Daphne genkwa* extract, fraction thereof, or compound isolated from the same | 10 mg |
| Crystalline cellulose | 3 mg |
| Lactose | 14.8 mg |
| Magnesium stearate | 0.2 mg |

Capsules were prepared by mixing all the above components, which were filled in gelatin capsules according to the conventional method for preparing capsules.

<1-4> Preparation of Liquid Formulations

| | |
|---|---|
| *Daphne genkwa* extract, fraction thereof, or compound isolated from the same | 20 mg |

-continued

| | |
|---|---|
| Isomerized sugar | 10 g |
| Mannitol | 5 g |
| Purified water | proper amount |

All the above components were dissolved in purified water. After adding lemon flavor, total volume was adjusted to be 100 ml by adding purified water. Liquid formulations were prepared by putting the mixture into brown bottles and sterilizing thereof by the conventional method for preparing liquid formulations.

<1-5> Preparation of Injectable Solutions

| | |
|---|---|
| *Daphne genkwa* extract, fraction thereof, or compound isolated from the same | 10 μg /ml |
| Weak HCl BP until | pH 7.6 |
| Injectable NaCl BP up to | 1 ml |

The ethanol mixture extract was dissolved in proper volume of injectable NaCl BP. pH of the prepared solution was regulated as 7.6 by using weak HCl BP. The volume was adjusted by using injectable NaCl BP. The solution was well mixed and filled in 5 ml type I transparent glass ampoules. The ampoules were sealed by melting the glass of opening, followed by autoclave at 120° C. for at least 15 minutes for sterilization.

MANUFACTURING EXAMPLE 2

Preparation of Foods

Foods containing the *Daphne genkwa* extract, the fraction thereof, or the compound isolated from the same of the present invention were prepared as follows.

<2-1> Preparation of Flour Foods 0.5~5.0 weight part of the *Daphne genkwa* extract, the fraction thereof, or the compound isolated from the same of the present invention was added to flour. Health enhancing foods such as bread, cake, cookies, crackers and noodles were prepared with the flour mixture according to the conventional method.

<2-2> Preparation of Dairy Products

5~10 weight part of the *Daphne genkwa* extract, the fraction thereof, or the compound isolated from the same of the present invention was added to milk. Health enhancing dairy products such as butter and ice cream were prepared with the milk mixture according to the conventional method.

<2-3> Preparation of Sun-Sik

Brown rice, barley, glutinous rice and Yulmu (Job's tears) were gelatinized according to the conventional method, dried and pulverized to obtain 60-mesh powders.

Black soybean, black sesame and wild sesame were steamed and dried according to the conventional method and pulverized to obtain 60-mesh powders.

The *Daphne genkwa* extract, the fraction thereof, or the compound isolated from the same of the present invention was concentrated under reduced pressure, spray-dried and pulverized to obtain 60-mesh dry powders.

Sun-Sik was prepared by mixing the dry powders of the grains, seeds and the *Daphne genkwa* extract, the fraction thereof, or the compound isolated from the same according to the below ratio.

Grains (brown rice: 30 weight part, Yulmu: 15 weight part, barley: 20 weight part), Seeds (wild sesame: 7 weight part, black soybean: 8 weight part, black sesame: 7 weight part), Dry powders of the *Daphne genkwa* extract, the fraction thereof, or the compound isolated from the same of the present invention (3 weight part),

*Ganoderma lucidum* (0.5 weight part),

*Rehmannia glutinosa* (0.5 weight part)

<2-4> Preparation of Health Supplement Foods

| | |
|---|---|
| *Daphne genkwa* extract, fraction thereof, or compound isolated from the same | 100 mg |
| Vitamin complex | proper amount |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinic acid amide | 1.7 mg |
| Folic acid | 50 μg |
| Calcium pantothenate | 0.5 mg |
| Minerals | proper amount |
| Ferrous sulfate | 1.75 mg |
| Zinc oxide | 0.82 mg |
| Magnesium carbonate | 25.3 mg |
| Potassium phosphate monobasic | 15 mg |
| Potassium phosphate dibasic | 55 mg |
| Potassium citrate | 90 mg |
| Calcium carbonate | 100 mg |
| Magnesium chloride | 24.8 mg |

Vitamins and minerals were mixed according to the preferable composition rate for health food. However, the composition rate can be adjusted. The constituents were mixed according to the conventional method for preparing health food (ex. granules, etc) and then the composition for health food was prepared according to the conventional method.

MANUFACTURING EXAMPLE 3

Preparation of Health Beverages

| | |
|---|---|
| *Daphne genkwa* extract, fraction thereof, or compound isolated from the same | 100 mg |
| Citric acid | 100 mg |
| Oligosaccharide | 100 mg |
| Maesil (*Prunus mume*) Extract | 2 mg |
| Taurine | 100 mg |
| Purified water up to | 500 ml |

The above constituents were mixed according to the conventional method for preparing health beverages. The mixture was heated at 85° C. for 1 hour with stirring and then filtered. The filtrate was loaded in 1 l sterilized containers, which were sealed and sterilized again, stored in a refrigerator until they would be used for the preparation of a composition for health beverages.

The constituents appropriate for favorite beverages were mixed according to the preferred mixing ratio but the composition ratio can be adjusted according to consumer characteristics, purpose of use, regional and national preferences, etc.

MANUFACTURING EXAMPLE 4

Preparation of Cosmetics

<4-1> Preparation of Emollient Toilet Water (Skin)

Emollient toilet water for atopic skin comprising the *Daphne genkwa* extract, the fraction thereof, or the compound isolated from the same of the present invention was prepared by mixing all the components shown in [Table 2] by the conventional method for preparing cosmetics.

TABLE 2

| Component | Content (weight %) |
|---|---|
| *Daphne genkwa* extract, fraction thereof, or compound isolated from the same | 0.1~30% |
| 1,3-butyleneglycol | 3.0 |
| Glycerine | 5.0 |
| Polyoxyethylene (60) Hydrogenated castor oil | 0.2 |
| Ethanol | 8.0 |
| Citric acid | 0.02 |
| Sodium citrate | 0.06 |
| Antiseptic | Proper amount |
| Flavor | Proper amount |
| Purified water | To 100 |

<4-2> Preparation of Nutritive Toilet Water (Lotion)

Nutritive toilet water for atopic skin comprising the *Daphne genkwa* extract, the fraction thereof, or the compound isolated from the same of the present invention was prepared by mixing all the components shown in [Table 3] by the conventional method for preparing cosmetics.

TABLE 3

| Component | Content (weight %) |
|---|---|
| *Daphne genkwa* extract, fraction thereof, or compound isolated from the same | 0.1~30% |
| 1,3-butyleneglycol | 8.0 |
| Glycerine | 5.0 |
| Squalane | 10.0 |
| Polyoxyethylene sorbitan monooleate | 2.0 |
| Guaiac oil | 0.1~30% |
| 1,3-butyleneglycol | 3.0 |
| Glycerine | 5.0 |
| Polyoxyethylene (60) Hydrogenated castor oil | 0.2 |
| Ethanol | 8.0 |
| Citric acid | 0.02 |
| Sodium citrate | 0.06 |
| Antiseptic | Proper amount |
| Flavor | Proper amount |
| Purified water | To 100 |

<4-3> Preparation of Essence

Essence for atopic skin comprising the *Daphne genkwa* extract, the fraction thereof, or the compound isolated from the same of the present invention was prepared by mixing all the components shown in [Table 4] by the conventional method for preparing cosmetics.

TABLE 4

| Component | Content (weight %) |
|---|---|
| *Daphne genkwa* extract, fraction thereof, or compound isolated from the same | 0.1~30% |
| Sitostorol | 1.7 |
| Polyglyceryl2-olate | 1.5 |
| Ceramide | 0.7 |
| Ceteareth-4 | 1.2 |
| Cholesterol | 1.5 |
| Dicetyl phosphate | 0.4 |
| Concentrated glycerin | 5.0 |
| Carboxyvinylpolymer | 0.2 |
| Xanthan gum | 0.2 |
| Antiseptic | Proper amount |
| Flavor | Proper amount |
| Purified water | To 100 |

<4-4> Preparation of Cleanser (Cleansing Foam)

Cleanser for atopic skin comprising the *Daphne genkwa* extract, the fraction thereof, or the compound isolated from the same of the present invention was prepared by mixing all the components shown in [Table 5] by the conventional method for preparing cosmetics.

TABLE 5

| Component | Content (weight %) |
|---|---|
| *Daphne genkwa* extract, fraction thereof, or compound isolated from the same | 0.1~30% |
| N-acyl sodium glutamate | 20.0 |
| Glycerine | 10.0 |
| PEG-400 | 15.0 |
| Propyleneglycol | 10.0 |
| POE(15) oleylalcoholether | 3.0 |
| Laurin derivative | 2.0 |
| Methylparabene | 0.2 |
| EDTA-4Na | 0.03 |
| Flavor | 0.2 |
| Purified water | To 100 |

<4-5> Preparation of Nutritive Cream

Nutritive cream for atopic skin comprising the *Daphne genkwa* extract, the fraction thereof, or the compound isolated from the same of the present invention was prepared by mixing all the components shown in [Table 6] by the conventional method for preparing cosmetics.

TABLE 6

| Component | Content (weight %) |
|---|---|
| *Daphne genkwa* extract, fraction thereof, or compound isolated from the same | 0.1~30% |
| Vaseline | 7.0 |
| Liquid paraffin | 10.0 |
| Wax | 2.0 |
| Polysorbate 60 | 2.5 |
| Sorbitan sesquioleate | 1.5 |
| Squalane | 3.0 |
| Propyleneglycol | 6.0 |
| Glycerine | 4.0 |
| Triethanolamine | 0.5 |
| Xanthan gum | 0.5 |
| Tocophenylacetate | 0.1 |
| Flavor, Antiseptic | Proper amount |
| Purified water | To 100 |

<4-6> Preparation of Massage Cream

Massage cream for atopic skin comprising the *Daphne genkwa* extract, the fraction thereof, or the compound isolated from the same of the present invention was prepared by mixing all the components shown in [Table 7] by the conventional method for preparing cosmetics.

TABLE 7

| Component | Content (weight %) |
|---|---|
| *Daphne genkwa* extract, fraction thereof, or compound isolated from the same | 0.1~30% |
| Propyleneglycol | 6.0 |
| Glycerine | 4.0 |
| Triethanolamine | 0.5 |
| Wax | 2.0 |
| Tocophenylacetate | 0.1 |
| Polysorbate 60 | 3.0 |
| Sorbitan sesquioleate | 2.5 |
| Cetearyl alcohol | 2.0 |
| Liquid paraffin | 30.0 |
| Xanthan gum | 0.5 |
| Flavor, Antiseptic | Proper amount |
| Purified water | To 100 |

<4-7> Preparation of Pack

Pack for atopic skin comprising the *Daphne genkwa* extract, the fraction thereof, or the compound isolated from the same of the present invention was prepared by mixing all the components shown in [Table 8] by the conventional method for preparing cosmetics.

TABLE 8

| Component | Content (weight %) |
|---|---|
| *Daphne genkwa* extract, fraction thereof, or compound isolated from the same | 0.1~30% |
| Propyleneglycol | 2.0 |
| Glycerine | 4.0 |
| Polyvinylalcohol | 10.0 |
| Ethanol | 7.0 |
| PEG-40 hydrogenated castor oil | 0.8 |
| Triethanolamine | 0.3 |
| Flavor, Antiseptic | Proper amount |
| Purified water | To 100 |

The present invention is not limited in the above illustrated examples, and can be modified or changed by those in the art. The present invention can also be applied to various types of cosmetics including color cosmetics, and can be used for the preparation of ointment or drugs for light application on human skin considering the effect. The said criteria is all included in the spirit and scope of the present invention as set forth in the appended Claims.

What is claimed is:

1. A method for treating atopy comprising administering to a subject in need thereof a pharmaceutically effective amount of a purified compound of Formula 1:

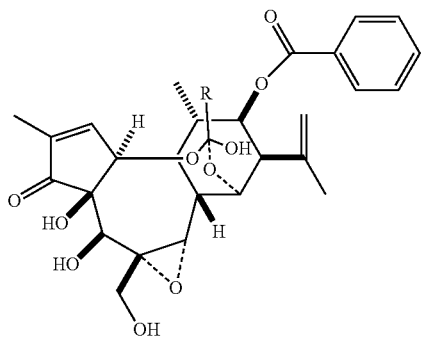

[Formula 1]

wherein, R is —$C_6H_5$ or —CH=CHCH=CH$(CH_2)_4$CH$_3$.

2. The method for treating atopy according to claim 1, wherein the compound of formula 1 is isolated from an extract of *Daphne genkwa*.

3. The method for treating atopy according to claim 1, wherein the compound of formula 1 maintains homeostasis of atopic skin by inducing the secretion of type I cytokine.

* * * * *